(12) United States Patent
Franzen et al.

(10) Patent No.: US 7,615,343 B2
(45) Date of Patent: Nov. 10, 2009

(54) ELECTRICAL READOUT OF THE BINDING OF ANALYTE MOLECULES TO PROBE MOLECULES

(75) Inventors: Jochen Franzen, Bremen (DE); Hans-Jakob Baum, Achim (DE)

(73) Assignee: Bruker Daltonik, GmbH, Bremen (DE)

( * ) Notice: Subject to any disclaimer, the term of this patent is extended or adjusted under 35 U.S.C. 154(b) by 368 days.

(21) Appl. No.: 10/824,656

(22) Filed: Apr. 14, 2004

(65) Prior Publication Data

US 2004/0235028 A1 Nov. 25, 2004

(30) Foreign Application Priority Data

Apr. 29, 2003 (DE) .................. 103 19 155

(51) Int. Cl.
 C12Q 1/68 (2006.01)
 C12P 19/34 (2006.01)
 C07H 21/02 (2006.01)
 C07H 21/04 (2006.01)
 C12Q 1/00 (2006.01)
(52) U.S. Cl. .................. 435/6; 435/91.2; 536/24.3; 536/24.33; 204/403.03
(58) Field of Classification Search .................. None
 See application file for complete search history.

(56) References Cited

U.S. PATENT DOCUMENTS

| | | | |
|---|---|---|---|
| 4,219,335 A | | 8/1980 | Ebersole |
| 4,822,566 A | | 4/1989 | Newman |
| 5,284,748 A | | 2/1994 | Mroczkowski et al. |
| 5,292,423 A | * | 3/1994 | Wang .................. 204/434 |
| 5,922,537 A | | 7/1999 | Ewart et al. |
| 6,207,369 B1 | * | 3/2001 | Wohlstadter et al. ......... 435/6 |
| 6,391,558 B1 | * | 5/2002 | Henkens et al. ............ 435/6 |
| 6,548,311 B1 | * | 4/2003 | Knoll .................. 436/524 |
| 2002/0028441 A1 | | 3/2002 | Hintsche et al. |

FOREIGN PATENT DOCUMENTS

| | | |
|---|---|---|
| DE | 197 51 706 A1 | 11/1997 |
| DE | 198 60 547 C1 | 12/1998 |
| WO | WO 90/05300 A1 | 5/1990 |
| WO | WO 97/45740 A1 | 12/1997 |
| WO | WO 9927367 A1 * | 6/1999 |
| WO | WO 00/11473 A1 | 3/2000 |
| WO | WO 00/77523 A1 | 12/2000 |
| WO | WO 01/13432 A1 | 2/2001 |
| WO | WO 02/31504 A1 | 4/2002 |
| WO | WO 02054052 A1 * | 7/2002 |
| WO | WO 03/031979 A1 | 4/2003 |

OTHER PUBLICATIONS

Wang J et al 'Metal nanoparticle-based electrochemical stripping potentiometric detection of DNA hybridization.' Anal Chem. Nov 15, 2001;73(22):5576-81.*
Town R.M. 'Potentiometric stripping analysis and anodic stripping voltammetry for measurement of copper(II) and lead(II) complexation by fulvic acid: A comparative study' Electroanalysis, 1997, 9, No. 5, p. 407-415.*
Jaya S et al 'Galvanic Stripping—A Simple and Versatile Approach to Trace Analysis' Analytical Letters, vol. 18 Issue 12 1985, pp. 1441-1456.*
Jaya et al 'Galvanic stripping determination of sub-microgram amounts of cadmium in high purity zinc materials' Analyst 1987, 112, pp. 1713-1715.*
Jaya et al 'Reductive galvanic stripping determination of lead' Analyst, 1987, 112, 955-958.*
Korri-Youssoufi, et al., "Electrochemical biosensing of DNA hybridization by ferrocenyl groups functionalized polypyrrole", Analytica Chimica Acta, vol. 469, pp. 85-92, 2002.
Park, et al., "Array-Based Electrical Detection of DNA with Nanoparticle Probes", Science, vol. 295, pp. 1503-1506, 2002.
Cai, et al., "Electrochemical detection of DNA hybridization based on silver-enhanced gold nanoparticle label", Analytica Chimica Acta, vol. 469, pp. 165-172, 2002.
British Search Report, Sep. 17, 2004.

* cited by examiner

Primary Examiner—Stephen Kapushoc
(74) Attorney, Agent, or Firm—Law Offices of Paul E. Kudirka

(57) ABSTRACT

The invention relates to the detection of the binding of analyte molecules, for example biopolymer molecules, to immobilized capture substance molecules. The invention consists in using semiconductor wafers (chips) with electrical circuits in spatial proximity to a surface area coated with capture substance molecules and loading the binding of the analyte molecules to the capture substance molecules with co-bound electrically conductive nanoparticles so that the nanoparticles can act upon the electrical circuits either through changes in the electrical stray capacitance or by generating electric currents, thus making the binding of the analyte molecules electronically detectable.

12 Claims, 1 Drawing Sheet

ELECTRICAL READOUT OF THE BINDING OF ANALYTE MOLECULES TO PROBE MOLECULES

FIELD OF THE INVENTION

The invention relates to the detection of the binding of analyte molecules, for example biopolymer molecules, to immobilized capture substance molecules.

BACKGROUND OF THE INVENTION

Today, we find a broad field of so-called chip arrays with covalently attached capture substance molecules for detecting affinity binding biopolymer molecules. The capture substance molecules bound to the array fields can be DNA molecules ("DNA chips"), protein molecules ("protein chips") or other types of molecule which can exhibit affinity binding. In the following, the biopolymer molecules will be termed "analyte molecules", the capture substance molecules on the chip fields simply as "probe molecules". The hybridisation or affinity binding of the analyte molecules to the probe molecules takes place using solutions in which target analyte molecules can occur, the solutions being in direct contact with the coated chip surface.

These chip arrays with probe molecules are used to study the binding characteristics (for example the study of possible cross reactions in the case of antibody binding), but especially they serve for the selective capture of analyte molecules from body fluids and hence for the qualitative and quantitative analysis of these analyte molecules. In some cases, for example for the detection of characterizing DNA strands of infection pathogens, the analyses are limited to simple statements as to the presence or absence of the infectious pathogens. The multiplicity of probe fields on the chip arrays means that in a sample with body fluids, the presence of one or more from many different types of infectious pathogens can be simultaneously detected.

The analytical methods with such chip arrays are also termed cell-based assays; the method itself is often termed "screening".

The chip arrays can be manufactured from semiconductor material such as silicon wafers, but any other type of wafer shaped materials can form the base to be coated with probe molecules. Different types of glass, metal or even plastics can be used for this. Semiconductors possess the advantage that electrical circuits can be incorporated into them, using microfabrication methods.

Only a small number of methods have so far been introduced as prior art for the detection of the binding of analyte molecules to probe molecules and they are only described very briefly here.

Detection of the binding is, for example, possible by using fluorescent dyes additionally bound to the analyte molecules; such methods require laser scanners or fluorescence microscopes. These instruments and methods are expensive mainly because the necessary (patented) fluorescent dyes are responsible for high consumable costs.

Mass spectrometric detection of the affinity bound analyte molecules, for example with ionization by matrix-assisted laser desorption (MALDI) after the addition of the appropriate matrix substances, is expensive because it requires a mass spectrometer. Consumable costs are restricted to the chip costs. Mass spectrometric detection does, however, have the advantage that it also provides additional confirmation of the identity of the analyte molecules by virtue of their mass.

A further method, currently under development, consists of the simultaneous binding of the analyte molecules and larger masses, for example using nanoparticles, onto suitable oscillators to detect the affinity binding by means of surface acoustic waves whose frequency depends on the mass of the coating.

The method of plasmon resonance spectrometry, which is also used to detect the affinity binding of analyte molecules to probe molecules, requires somewhat larger areas for the flat reflection of the light, so that it has not yet proved possible to produce arrays with large numbers of fields for this type of detection. The advantages lie in the fact that this method can also measure the kinetics of the binding process.

The use of chip arrays which can simultaneously detect the presence or absence of hundreds or thousands of different types of analyte substances by coating them with different kinds of probe molecules is predicted to have a great future. The existing readout methods are still too complicated, however. There is therefore a need for a simple method of reading out the binding of the analyte molecules as directly as possible. A simple readout method for affinity binding would not only be of interest for chip arrays with many fields, but also for individual fields which can be charged in succession with different types of ligand, for example.

SUMMARY OF THE INVENTION

A central idea of the invention is to bind electrically conductive nanoparticles together with the analyte substances to the surface-bound probe molecules, the nanoparticles acting upon nearby electronic circuits by changing the capacitance or by current generation, the latter after making an electrical contact, and hence making the binding measurable. The electronic circuits are preferably incorporated into semiconductor surfaces and are termed "circuit surfaces" below.

The probe molecules can be located on the circuit surface itself; they can also be located on a surface opposite the semiconductor surface. This surface will be termed "countersurface" in the following. It is preferable if these two surfaces, circuit surface and countersurface, are designed to be flat and parallel to each other and, in some cases, the countersurface should be movable towards the circuit surface.

The nanoparticles should be electrically conductive, for example by means of a metal core or a metal surface. The nanoparticles can then exert an electrical (not mechanical, as is the case with surface acoustic waves) effect on the electrical circuits of the circuit surface. As a result of this effect, the binding of analyte molecules to the probe molecules can be read out by changing the behavior of the circuits. The electrical effect of the nanoparticles on the circuits can occur capacitively or by current generation; in the latter case the current flow is caused by the nanoparticles, e.g. by means of an electrochemically generated voltage after setting up a contact with contact spots on the circuit surfaces, or by making contact between circuit surface contact spots and countersurface spots under some voltage.

One possibility is that the nanoparticles can already be bound to the analyte substances. It is favorable, however, to first bind the analyte molecules to the probe molecules as a first step, and to follow this with a second step in which the nanoparticles, which are also coated with capture substances, are bound to the now immobilized analyte substances via a second affinity binding. For the sake of clarity, these capture molecules on the nanoparticles are termed "adhesion molecules" below. The second step of this multiple step method can be carried out by adding further liquid containing the nanoparticles coated with adhesion molecules, or by exchanging the liquids. For the measurement it may be advisable, in a third step, to remove the unbound nanoparticles again by exchanging the liquids.

The conductive nanoparticles influence, either in the liquid state or in a state after drying, the electrical ambient capacitance on the circuits and so bring about a measurable change to the behavior of the electrical circuit. As an electrolyte, the liquid always has a certain conductivity, and so the change in the capacitance in the liquid can only be measured with a sufficiently high frequency because the free movement of the ions in the liquid is then limited by the restricted ion mobility, while the electron stream in the nanoparticle can flow almost unhindered with very small inertia only.

If the countersurface cautiously presses the nanoparticles against certain contact spots of the circuit surface, it is possible to create a current directly between the countersurface and the contact spots contacted by the nanoparticles, thus indicating the areas which are covered by nanoparticles.

The nanoparticles can also be metallized with a noble metal such as silver; with added electrolyte liquid containing a little soluble silver salt, and a counterelectrode spot in a base metal such as zinc; the nanoparticles then form a galvanic element, on a part of the circuit surface, said element creating a potential between the nanoparticles and counterelectrode spot on the circuit surface. To enable a current to flow in the circuit surface, it is necessary to bring the nanoparticles into electrically conductive contact with contact spots near to the counterelectrode spots on the circuit surface.

If, for example, the core of the nanoparticle is magnetizable, then a magnetic force can be used to press the nanoparticle into contact with the contact spots on the circuit surface (away from the counterelectrode spots). A current then flows through the circuit surface from the contact spots to the counterelectrode spots, and this current can act upon the circuits of the circuit surface, for example on the control grid of field effect transistors.

N-type chain molecules can also be arranged between circuit surface and nanoparticle, for example by binding long polyacetylene chains (a polyene), covalently attached at one end, between the probe molecules so that the voltage potential of the nanoparticles acts directly upon the control grid of a field effect transistor through the n-type molecules. This type of effect is very sensitive, even a single, bound nanoparticle can generate a measurable effect.

If the probe molecules are located on the countersurface opposite the circuit surface, then the complete countersurface can also be pressed onto the circuit surface in order to create the contacts of the circuit surface with the nanoparticles. If electrochemical cells are thereby formed to create the currents, the countersurface with the probe fields should preferably consist of an insulating material; alternatively, the conductive substrates of the probe fields should at least be isolated from each other.

For the detection of certain DNA sequences in the analyte liquid, a PCR reaction can also be carried out first. This can also take place in a chamber, of which one wall is formed by the circuit surface. The other wall can be a wall made of glass or semiconductor into which appropriate heating elements for the heating cycles of the PCR reaction are integrated. The PCR reaction can be integrated into the first step of a multiple step process, for example.

Magnetizable nanoparticles ("magnetic beads") can be manipulated via external inhomogeneous magnetic fields by virtue of their magnetizable core. They can be removed from the probe fields, for example, in the case of purely adhesion binding but not in the case of affinity binding of the adhesion molecules, which have considerably higher binding energies.

In addition, the liquid with the nanoparticles can be stirred by magnetic eddy fields in order to assist the extremely slow diffusion motion of the nanoparticles (which leads to extremely slow reaction speeds of the affinity binding to the immobilized analyte molecules) by means of all sorts of eddy currents in the liquid.

BRIEF DESCRIPTION OF THE DRAWINGS

The above and further advantages of the invention may be better understood by referring to the following description in conjunction with the accompanying drawings in which.

DETAILED DESCRIPTION

Figures 1, 2:
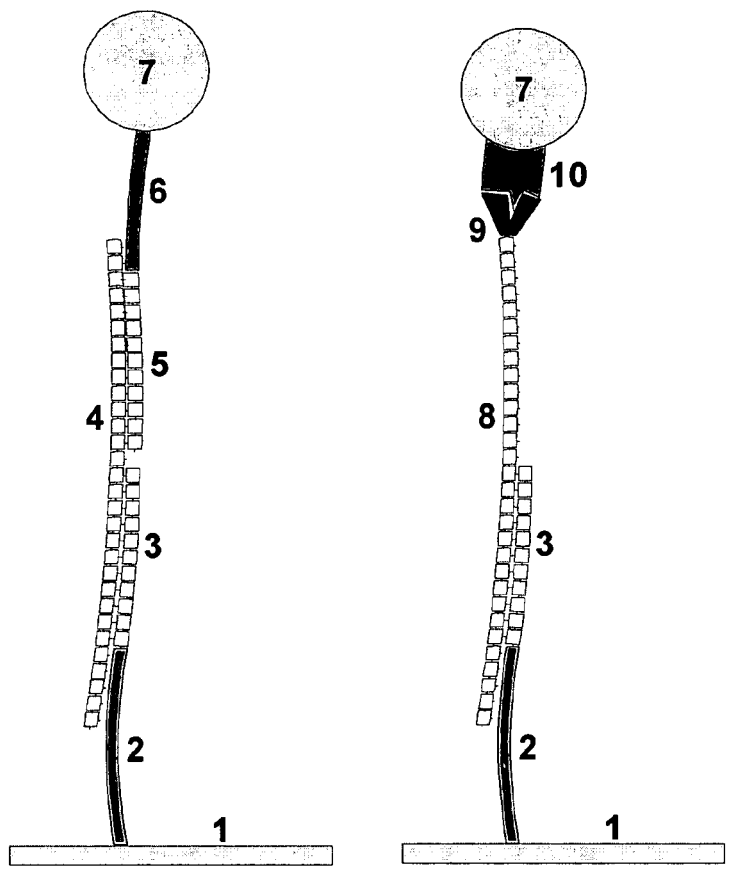
FIG. 1, along with FIG. 2 illustrates the indirect binding of a nanoparticle (7) to a surface (1)
FIG. 2 shows the nanoparticle (7) of FIG. 1, which is coated with strepatividin (10), bound to the biotin group (9) of the analyte molecule (8)

The invention involves binding electrically conductive nanoparticles together with the analyte molecules to immobilized probe molecules, and allowing the nanoparticles to exert electrical effects on electrical circuits arranged nearby by means of current generation or a capacitance change. In FIG. 1, a DNA probe (3) is covalently attached to the surface (1) by means of a flexible bridge (2). An analyte molecule (4) binds to the DNA probe (3) by hybridization. Via a second flexible bridge (6), the nanoparticle (7) carries the adhesion molecule (5), which binds to the analyte molecule (4) next to the probe (3). The nanoparticles can have diameters in the range from 20 nanometers to around 10 micrometers; in individual cases, higher or lower than this. The circuits are usually based on silicon wafers, into which the circuits are integrated using microfabrication methods such as ion implantation and ion etching or also mask controlled manipulations. The nanoparticles exert a capacitive or current generating (after electrochemical voltages and/or contacts have been formed) electrical effect on the electronic circuits, so that a change in the control behavior of the circuits makes the binding of analyte molecules via the co-bound nanoparticles measurable and hence simple to read out.

Herein, the target molecules, for example biopolymers, whose binding to the surface-bound capture molecules is to be measured, are termed "analyte molecules." The surface-bound capture molecules are referred to as "probe molecules," thereby distinguishing them from the capture molecules on the nanoparticles. A surface which is coated with the same type of probe molecules is called a "probe field". The probe fields can be located on the "circuit surface" or on a "countersurface" positioned opposite the circuit surface. The capture molecules on the nanoparticles, which are used in multiple step methods, are termed "adhesion molecules" herein for the sake of distinction, even though they can capture molecules with the same types of binding functions as the probe molecules. The term "covalent attachment" means the primary valency bonds (80 to 550 kJ/mol), while "affinity binding" refers to the secondary valency bonds (8 to 20 kJ/mol, associations, dipole-dipole bonds, van-der-Waals bonds, hydrogen bridge bonds etc). The methods described here are usually used to measure the affinity binding of analyte molecules to covalently attached probe molecules on probe fields. The affinity binding is normally easy to reverse so that the probe fields can be used again.

Below it is discussed how the nanoparticles in the physicochemical part of the method are bound together with the affinity binding analyte molecules to surfaces in spatial proximity to the circuit surface, using a method which is already known in principle. It is also described how the nanoparticles on the circuits can have an electrical effect in order to effectuate the readability of the affinity binding in the electronic measuring part of the method. The analyte substances can be already bound to the nanoparticles before they react with the probe molecules.

The following example has the objective of examining the binding behavior of a protein molecule examined as a target. For tests with hundreds of relevant types of ligands from libraries, the ligands can all already be bound to nanoparticles. The ligands can, for example, be fed one after the other to an electronic chip with directly covalently attached target molecules which here act as probe molecules. This is followed in each case by the measurement of a possible binding of the ligands. Since the binding of the ligands is not covalent but only by reversible affinity, the ligands can be detached again afterwards. The chip surface is then free for testing of the next ligands. This test can easily be automated.

For circuit surfaces (or countersurfaces located opposite) with many probe fields coated with different probe molecules, it seems to be favorable to employ a multiple step method. In a first step the analyte substances are bound to the probe substances, and in a second step the nanoparticles, which are coated with adhesion molecules, are bound to the now immobilized analyte substances via a second affinity binding. After the first step, this multiple step method can be carried out by adding more liquid containing the nanoparticles or by exchanging the liquids. For the measurement it is favorable if not necessary, in a third step, to remove the unbound nanoparticles again by exchanging the liquids and by appropriate washing. A fourth step can follow with partial or complete drying.

FIG. 1 depicts an example of a multiple step method which relates to the detection of DNA hybridizations: DNA strands can be covalently attached to the probe fields (1) as probe molecules (3) (frequently termed "probes"), said DNA strands (3) binding corresponding complementary strands of analytical DNA (4) from the analyte solution. Such a probe (3) would normally be located on a flexible stem (2) from a polymer molecule covalently attached on one side to the fixed surface (1) and on the other to the DNA probe (3). This arrangement makes it easier to hybridize the analyte molecules (4) of the analyte liquid. To effect the hybridization, an optimum temperature is set which makes the diffusion of the analyte molecules (4) easier, while allowing the hybridization with the correct complementary strands, in order to prevent hybridization with those complementary strands whose sequence does not completely correspond to that of the probes, i.e., with those which contain defects. After hybridization, the analyte solution is exchanged for a solution which contains the nanoparticles. Covalent DNA strands (5) are bound as adhesion molecules to these nanoparticles (7), again via flexible bridge polymers (6), and these DNA strands (5) hybridize adjacent to the DNA probes (3) on the now immobilized DNA analyte molecules (4). As a result of the slow diffusion of the nanoparticles, one must allow a relatively long time for the hybridization, although the process can be accelerated by careful stirring. The nanoparticles are bound indirectly onto the chip surface by the process of double hybridization. This method is known in principle.

This method is particularly suitable for species recognition of animals, plants and microorganisms. With this method, the target species is determined by using characteristic sequences of their DNA (or RNA) as probe sequences on the probe fields and as adhesion substance sequences on the nanoparticles. It is thus possible to recognize infectious pathogens, for example. It is possible to determine if the meat in a sausage comes from a cow, horse, donkey, giraffe or kangaroo. Genetically engineered modifications of plants or animals can be established if the modification sequences are known.

The isolation and preparation of the DNA may be done using known techniques. In order to facilitate the diffusion of the very long DNA strands and the dehybridization of the DNA double strands before the analysis, the DNA can be digested by suitable enzymes (endonucleases) into shorter strands. On the other hand, suitable sections of the DNA can be amplified by polymerase chain reactions (PCR) before being fed to the analysis by the chips.

With PCR-amplified DNA, the primers used for amplification can also be terminated to one end with biotin groups (during the manufacture of the primer oligos the primers are usually immobilized via a biotin binding so that for an order of biotinylated primers no additional costs are incurred). As shown in FIG. 2, the biotin group (9) enters with the primers terminally into the amplified analyte molecules (8). After the hybridization of the analyte molecules (8) on the probe molecules (3), bound covalently via a bridge (2) on the chip surface (1), nanoparticles (7) can then be added which, in a known manner, are coated with streptadivin groups (10) by covalent attachment to the nanoparticle surface. Since the streptadivin (10) immediately binds with the biotin (9), the nanoparticles (7) are thus bound indirectly to the chip surface (1). Instead of the known biotin-streptadivin binding pair, any other binding pairs can, of course, be used.

Another example of a multiple step method relates to the detection of certain proteins in the analyte liquid. Here, use is made of antibodies which specifically affinity bind certain proteins to the surface via so-called binding motifs. In this method, antibodies are bound as probe molecules to the probe fields, and the antibodies bind all proteins from the analyte liquid which possess a corresponding binding motif. The nanoparticles then added in the next step also have antibodies bound as adhesion molecules, but this time they are bound to an opposing second binding motif of the already bound proteins. It is favorable if the antibodies sitting on the nanoparticles as adhesion molecules are less specific and selective and bind to a large number of proteins, but not to the antibodies applied as probe molecules. In this case also, the nanoparticles are bound indirectly to the surface of the probe fields.

In the case of proteins it is also possible, if so desired, to produce an extremely high degree of selectivity, and thus very certain detection of the target analyte protein, by means of a doubly selective binding with selective probe molecules and selective adhesion molecules.

In particular, the nanoparticles can also contain a magnetizable core ("magnetic beads"), allowing them to be manipulated by external inhomogeneous magnetic fields. The nanoparticles can, for example, be removed from the probe fields by strongly inhomogeneous magnetic fields, for example in the case of adhesion capture rather than affinity binding with considerably higher binding energies. The washing of the probe fields and rinsing away of unbound nanoparticles can thus be assisted. In addition, the liquid with the nanoparticles can be stirred by magnetic eddy fields in order to assist the extremely slow diffusion motion of the nanoparticles, which leads to extremely slow reaction speeds of the affinity binding to the immobilized analyte molecules, by means of all sorts of magnetic eddy currents in the liquid. The nanoparticles can also be collected on an opposing wall if, for example, the liquid is to be changed without losing the nanoparticles.

The nanoparticles, which are henceforth immobilized by indirect binding to the surface of the probe fields, can act in different ways upon nearby circuits: by changing the ambient capacitance or by forming potential differences. The known mechanical effect produced by changing the frequency of surface acoustic waves will not be discussed here.

Both in the liquid state and in the state after drying, the conductive nanoparticles influence the electrical ambient capacitance on the circuits and can thus bring about a measurable change in the behavior of the electrical circuit. In the dry state the nanoparticles act like small additional capacitors on the circuits. Their effect can be measured, for example, by the detuning of high frequency circuits. The additional capacitance can play a significant role especially when a flat semiconductor surface with circuits is located relatively close to and opposite another flat surface which acts as a counterelectrode (which does not necessarily have to be identical to the above defined countersurface containing the probe fields) and the nanoparticles between semiconductor and counterelectrode generate a change in the circuit capacitances and hence a strong detuning of the RF circuits. In such a case, semiconductor surface and counterelectrode can form two parallel walls of a slit shaped vessel which initially contains the analyte liquid, then will be filled with the nanoparticle liquid, then with the washing liquid and finally with drying gas.

The nanoparticles can also be measured within the liquid by the change in the ambient capacitance. This requires a sufficiently high test frequency since at low frequencies the measurement is disturbed by the ion flow in the liquid to such a degree that the additional capacitance can no longer be measured. Only at sufficiently high frequencies is the ion current sufficiently hindered by the limited mobility of the ions in the liquid that the additional capacitance produced by the nanoparticles, with the electron current which flows almost unhindered through them, can be recognised by its effect on the circuits.

The nanoparticles can also be used to construct an electrochemical cell (a galvanic element) whose voltage acts on the circuits of the chip after coming into contact with them. An example is given in FIG. 3. For this purpose, the nanoparticles (14) can be metallized with a noble metal such a silver. With a suitable metal such as zinc on a counterelectrode spot (12) of the circuit surface (11) and the addition of a little silver nitrate to the liquid between circuit surface (11) and countersurface (16), a galvanic element is formed with a static circuit voltage of around 1.5 volts, the nanoparticles (14) forming the positive pole and the zinc coating (12) the negative. Here, zinc molecules go as positively charged zinc ions from the zinc spots (12) of the chip surface (11) into solution and bring about the precipitation of positively charged silver ions on the silver surface of the nanoparticles (14). There is a current of positive charges from the zinc (12) to the silver (14) until the complete voltage has been built up. This only requires an extremely small amount of silver nitrate because, overall, practically no current flows (only the so-called displacement current).

The potential between silvered nanoparticles (14) in the electrolyte liquid and galvanized counterelectrode spot (12) on the surface of the chip cannot directly affect the circuits on other points of the chip surface via induced mirror charges since the nanoparticles (14) are completely surrounded by ions of opposite polarity and appear voltageless to the outside in the liquid.

Figures 3, 4:
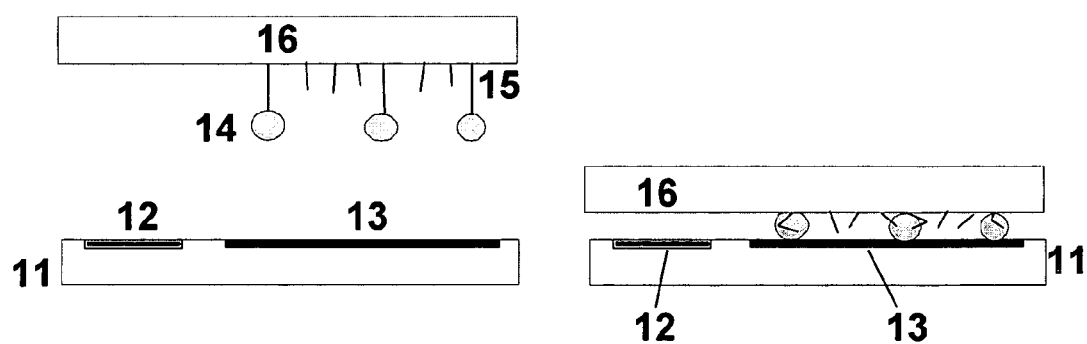
FIG. 3 illustrates the binding of nanoparticles (14) via analyte and probe molecules (15) to a countersurface (16) which is located opposite the contact spots (12) of a circuit surface (11), with a counterelectrode (12) for creating the electrochemical element.
FIG. 4 shows how the contact is made by pressing the nanoparticles (14) of FIG. 3 by the countersurface (16) onto the contact spots (12) of the circuit surface (11).

It is therefore necessary to create an electrically conductive contact of the nanoparticles to selected points on the circuits in the semiconductor surface, as seen in FIG. 4 where the nanoparticles are pressed against contact spot (13) of the circuit surface (11). A small current can then flow from this contact spot (13) to the zinc electrode (12). These special contact spots (13) on the chip circuits are here termed "contact spots". The contact spots (13) have a better conductivity than their surroundings and are connected with the zinc counterelectrode spots (12) via specially doped paths which can also be interrupted by control electrodes. The current flowing here, which again may be only a displacement current with very minor charge displacement, can be used to control the circuits, for example via the known inductive influence on the control grid electrodes of field effect transistors. This type of influence is very sensitive; just one single, bound nanoparticle can generate a measurable effect.

The covalent binding of the adhesion molecules on the silver surfaces of the nanoparticles via thio bonds may be by known means, and does not need to be described here.

In another embodiment, the countersurface (16) may be connected to a voltage source, and by pressing the nanoparticles (14) to the contact spot (13), the circuit is triggered in such a way as to measure the adhesion of nanoparticles, even without the formation of an electrochemical element, making the zinc counterelectrode spot (12) unnecessary.

An electrically conductive contact between nanoparticles (14) and contact spot (13) can be made in a number of ways: by the use of n-type chain molecules which are bound to the contact spots (13) of the chip surface, or by direct contact between the nanoparticles and the contact spot on the circuit surface, which can be created, for example, by magnetic or mechanical forces by bodies pressing against the contact spots, as discussed above in conjunction with FIG. 2. The electrical contact with the circuit surface can also be made by metal whiskers or other electrically conductive protrusions on the circuit surface or on the nanoparticle surface. Electrically conductive protrusions can also serve as contacts in combination with magnetic fields or mechanical forces.

The n-type molecules can be arranged in the probe fields (which are then identical with the contact points) between the probe molecules; they can also be located alone on the contact spots, in which case the probe fields then lie on surfaces situated opposite the countersurfaces as shown in FIG. 2. Chain molecules from the polyene group are suitable as electrically conductive molecules, these chain molecules consisting alternately of single and double bonds and whose $\pi$ electron clouds each overlap in such a way that a current of electrons can flow along the chain of molecules. They can be polymerized from acetylene, for example. If the chain molecules are bound to the circuit surface between the probe molecules, their length can be chosen in such a way that they stretch to the nanoparticles. For a distance of around 50 nanometers, around 300 chain links are needed. It is preferable if they are constructed by link-by-link synthesis on the circuit surface itself.

If the numerous circuits of a chip array are well insulated from each other and the circuits including the zinc counterelectrode spots and contact spots are well formed, then even if many galvanic cells are formed on the chip array, no mutual influencing of the circuits (crosstalk) is to be expected since the contact spots and the zinc counterelectrode spots are assigned to each other and the formation of a voltage on one circuit has no effect on other circuits even though the ion conducting liquid spreads evenly over all circuits.

If it should be expedient for a well separated measurement to separate the individual fields of the array on the circuit surface, then this can be achieved. It can be achieved that the electrolyte for the measuring phase no longer forms a continuous liquid layer which extends beyond the edges of the fields. This can be brought about by separating the individual array fields from one another by narrow channels whose walls are extremely hydrophobic. When the chips are covered with a large amount of aqueous liquid, these channels remain filled with air and the liquid forms a continuous volume. In this full liquid step the binding of the analyte molecules and then also the binding of the nanoparticles is undertaken. Removing most of the liquid splits open the channels; flat domes of liquid remain on the array fields, which are hydrophilic due to their coating of probe molecules and their partial coating of zinc. If silvered nanoparticles are located in these domes of liquid, then addition of silver salts produces a galvanic element, whereas in domes of liquid without nanoparticles no such electrochemical element is formed.

If the probe molecules are mounted on a countersurface located opposite the circuit surface, spatially distinct liquid fields can also be formed between circuit surface and countersurface.

The contact spots which are in contact with the nanoparticles (which are indirectly bound after binding reactions) via n-type chain molecules or via direct contact, can be located, for example, directly above the control grid electrodes for field effect transistors, whereas the galvanized part of the surface is located slightly to the side. After making contact, the contact spot then charges up to a voltage of around 1.5 volts. The electric field of this voltage affects the highly sensitive control grid electrode and controls the flow of current in the field effect transistor. The polarity of the galvanic element determines whether the transistor becomes conducting or not in the presence of the nanoparticles. If one wishes to generate an effect with opposite polarity, the nanoparticles as well can be coated with a base metal and the circuit surface covered with a noble metal. It is, of course, possible to use any pairs of metals from the electrochemical series for the formation of the galvanic element; the choice is limited, however, by the chemistry of the binding of organic adhesion molecules to the nanoparticles.

As has been stressed several times, it is not necessary that the probe molecules are located on the circuit surface itself; they can also be located on the countersurface. The indirectly bound nanoparticles here can also electrically affect the circuits of the circuit surface, either by changing the ambient capacitance or by generating a galvanic voltage. The contact between the nanoparticles and the circuit surface can then be achieved, for example, by pressing the whole countersurface with the nanoparticles onto the circuit surface. If galvanic element forming is used, then it is preferable if the countersurface, which is coated with probe molecules, is made of insulating material such as glass or plastic. The nanoparticles fixed onto this countersurface or the analyte molecules can also be released from their affinity partners by a reversible reaction, however, and then drawn by magnetic forces through the static liquid to the contact points on the circuit surface. As is known, the release of the affinity binding can be brought about by temperature increase, by changing the pH-value or by replacement reactions.

The contact points on the circuit surface can also be coated with n-type chain molecules which stretch to the nanoparticles on the probe fields of the countersurface.

For the detection of predetermined selected DNA sequences in the analyte liquid, a PCR reaction for the analyte sequences and their environment can be carried out first. This can take place directly in a chamber, one of whose walls is formed by the circuit surface. The other wall can be a wall of glass or semiconductor into which are integrated suitable heating elements for the heating cycles of the PCR reaction. The PCR reaction can be integrated into the first step of a multiple step method, for example.

In a PCR reaction it is also possible, for example, to lengthen both the probe sequences as primer on the chip surface and the adhesion sequences as primer on the nanoparticles with the help of suitable analyte molecules so that strand and complementary strand are formed in a complementary way. The nanoparticles can then be magnetically held in order to remove the superfluous analyte liquid with polymerase, buffers and nucleic acid triphosphate chips. This is followed by the carrying out of the hybridization of the extended probe sequences on the nanoparticles with the extended adhesion sequences on the surface of the chip.

While the invention has been shown and described with reference to a preferred embodiment thereof, it will be recognized by those skilled in the art that various changes in form and detail may be made herein without departing from the spirit and scope of the invention as defined by the appended claims.

What is claimed is:

1. A method for measuring the binding of analyte molecules to probe molecules, the method comprising the following steps:
    (a) providing a circuit surface having a spatially separated array of circuits, each circuit having an electronic detector circuit, a metal counterelectrode and a contact spot;
    (b) immobilizing a field of probe molecules in spatial proximity to each of the circuits wherein the probe molecules are the same for each circuit, but differ from circuit to circuit;
    (c) binding nanoparticles having a metal surface that forms an electrochemical series with the metal counterelectrode to the analyte molecules with adhesion molecules to form analyte structures;
    (d) placing the analyte structures in the vicinity of the probe molecules in order to facilitate binding of the analyte molecules to the probe molecules;
    (e) introducing an electrolyte adjacent the circuit surface so that in each circuit where nanoparticles are bound to proximal probe molecules via analyte molecules, the counterelectrode and the metal surfaces of the nanoparticles form electrodes of a galvanic cell;
    (f) in each circuit where nanoparticles are bound to the proximal probe molecules, physically moving the nanoparticles to establish an electrical contact between the metal surfaces on the nanoparticles and the contact spot; and
    (g) determining in which circuits galvanic cells have formed by detecting one of a galvanic cell current and a galvanic cell voltage between the counterelectrode and the contact spot with the electronic detector circuit, so that the spatial pattern of circuits in which galvanic cells have formed measures the binding of the analyte molecules to the probe molecules.

2. Method according to claim 1, wherein the probe molecules are immobilized by covalent binding and, in step (d), the analyte molecules bind by affinity to the probe molecules.

3. Method according to claim 1, wherein the electrical contact between the nanoparticles and the contact spot is established by electrically conductive n-type chain molecules that are bound to the contact spot.

4. Method according to claim 3, wherein the electrically conductive molecules are compounds of the polyene class.

5. Method according to claim 1, wherein the electrical contact between the nanoparticles and the contact spot is established by the nanoparticles touching the contact spot.

6. Method according to claim 5, wherein analyte molecules with nanoparticles bound thereto are bound to probe molecules immobilized on an insulating surface opposite the circuit surface, and the electrical contact of the nanoparticles with the contact spot is established by moving the insulating surface and the bound nanoparticles towards the circuit surface so that the nanoparticles touch the contact spot.

7. Method according to claim 5, wherein analyte molecules having magnetizable nanoparticles bound thereto are bound to probe molecules immobilized on a surface opposite the circuit surface; the linkages between the nanoparticles and the analyte molecules or the linkages between the analyte molecules and the probe molecules are broken; and the electrical contact of the now no longer immobilized nanoparticles with the contact spot of the circuit surface is established by an external magnetic field acting on the nanoparticles.

8. Method according to claim 5, wherein analyte molecules having magnetizable nanoparticles bound thereto are bound to probe molecules immobilized on the contact spot of the circuit surface, and electrical contact of the nanoparticles with the contact spot is established by the effect of an external magnetic field or by mechanical pressure of a countersurface on the nanoparticles.

9. Method according to claim 5, wherein the contact spot of each circuit, or the surface of the nanoparticles, is covered with electrically conductive protrusions.

10. Method according to claim 1, wherein DNA oligomers are used as probe molecules, the analyte molecules are amplified prior to step (d) by polymerase chain reactions (PCR) using a biotinylated primer, and the nanoparticles are coated with streptavid in, enabling binding of the nanoparticles to biotin groups of the analyte molecules by a biotin-streptavidin binding pair.

11. Method according to claim 10, wherein the analyte molecules are amplified prior to step (d) by polymerase chain reaction (POR) using a primer comprising a first member of a binding pair, and the nanoparticles are coated with a second member of said binding pair that binds to said first member, enabling binding of the nanoparticles to the analyte molecules.

12. Method according to claim 1, wherein the probe molecules are immobilized in spatial proximity to the electronic circuits on a countersurface, positioned opposite the circuit surface.

* * * * *